United States Patent
Kudo et al.

(10) Patent No.: US 12,367,620 B2
(45) Date of Patent: Jul. 22, 2025

(54) TRAINED MODEL GENERATION PROGRAM, IMAGE GENERATION PROGRAM, TRAINED MODEL GENERATION DEVICE, IMAGE GENERATION DEVICE, TRAINED MODEL GENERATION METHOD, AND IMAGE GENERATION METHOD

(71) Applicant: University of Tsukuba, Ibaraki (JP)

(72) Inventors: Hiroyuki Kudo, Tsukuba (JP); Kazuki Mori, Tsukuba (JP)

(73) Assignee: UNIVERSITY OF TSUKUBA, Tsukuba (JP)

( * ) Notice: Subject to any disclaimer, the term of this patent is extended or adjusted under 35 U.S.C. 154(b) by 289 days.

(21) Appl. No.: 17/909,998

(22) PCT Filed: Feb. 24, 2021

(86) PCT No.: PCT/JP2021/006833
§ 371 (c)(1),
(2) Date: Sep. 8, 2022

(87) PCT Pub. No.: WO2021/182103
PCT Pub. Date: Sep. 16, 2021

(65) Prior Publication Data
US 2023/0106845 A1    Apr. 6, 2023

(30) Foreign Application Priority Data
Mar. 11, 2020   (JP) .................. 2020-042154

(51) Int. Cl.
G06T 11/00    (2006.01)
A61B 6/00     (2024.01)
(Continued)

(52) U.S. Cl.
CPC ............. G06T 11/005 (2013.01); G06T 5/70 (2024.01); G06V 10/82 (2022.01); *G06T 2207/10081* (2013.01)

(58) Field of Classification Search
CPC ............... G06T 11/005; G06T 5/70; G06T 2207/10081; G06T 2211/436;
(Continued)

(56) References Cited

U.S. PATENT DOCUMENTS 11,112,480 B2 *   9/2021   Kartäusch .......... G01R 33/5611
11,315,221 B2 *   4/2022   Matsuura .............. G06F 18/214
(Continued)

FOREIGN PATENT DOCUMENTS

CN    107871332 A    4/2018
CN    110751701 A    2/2020
(Continued)

OTHER PUBLICATIONS

International Search Report and Written Opinion mailed on Apr. 20, 2021, received for PCT Application PCT/JP2021/006833, filed on Feb. 24, 2021, 10 pages including English Translation.
(Continued)

*Primary Examiner* — Bobbak Safaipour
*Assistant Examiner* — Joshua Chen
(74) *Attorney, Agent, or Firm* — XSENSUS LLP

(57) ABSTRACT

A trained model generation program causes a computer to implement a learning execution function of inputting first input image data representing a first input image generated by a first reconstruction method using compressed sensing and second input image data representing a second input image generated by a second reconstruction method different from the first reconstruction method to a machine learning device to execute machine learning, the second reconstruction method being an analytical reconstruction
(Continued)

method, and causing the machine learning device to generate a trained model, and a trained model acquisition function of acquiring trained model data indicating the trained model. Then, input image data representing an input image is input to the trained model to generate a reconstructed image with improved image quality.

10 Claims, 21 Drawing Sheets

(51) Int. Cl.
*G06T 5/60* (2024.01)
*G06T 5/70* (2024.01)
*G06V 10/82* (2022.01)

(58) Field of Classification Search
CPC . G06T 11/006; G06T 2211/441; G06V 10/82; A61B 6/52
See application file for complete search history.

(56) References Cited

U.S. PATENT DOCUMENTS

| | | | |
|---|---|---|---|
| 2019/0251713 A1* | 8/2019 | Chen | A61B 6/482 |
| 2019/0325621 A1 | 10/2019 | Wang et al. | |
| 2019/0353741 A1 | 11/2019 | Bolster, Jr. et al. | |
| 2019/0371018 A1 | 12/2019 | Ye et al. | |
| 2020/0294287 A1* | 9/2020 | Schlemper | G06T 3/60 |
| 2020/0311490 A1* | 10/2020 | Lee | G06T 5/60 |
| 2021/0012543 A1* | 1/2021 | Hein | G06T 11/008 |
| 2021/0118204 A1 | 4/2021 | Fu et al. | |

FOREIGN PATENT DOCUMENTS

| | | | |
|---|---|---|---|
| JP | 2018-134199 A | 8/2018 | |
| WO | 2016/033458 A1 | 3/2016 | |
| WO | WO-2017223560 A1 * | 12/2017 | A61B 5/00 |

OTHER PUBLICATIONS

Han et al., "Deep Residual Learning for Compressed Sensing CT Reconstruction via Persistent Homology Analysis", arXiv: 1611.06391v2, Nov. 25, 2016, 10 pages.

Ma et al., "Low dose CT reconstruction assisted by an image manifold prior", Medical Physics, arXiv: 1810.12255, Oct. 29, 2018, pp. 1-15.

European Search Report issued Mar. 5, 2024 in European Patent Application No. 21767498.5.

Yinsheng Li et al.: "Learning to Reconstruct Computed Tomography Images Directly From Sinogram Data Under A Variety of Data Acquisition Conditions", IEEE Transactions on Medical Imaging, IEEE, USA, vol. 38, No. 10, Oct. 1, 2019, pp. 2469-2481, XP011748202, ISSN: 0278-0062, DOI: 10.1109/TMI.2019.2910760.

Yongbo Wang et al: "Iterative quality enhancement via residual-artifact learning networks for low-dose CT", Physics in Medicine and Biology, Institute of Physics Publishing, Bristol GB, vol. 63, No. 21, Oct. 23, 2018, p. 215004, XP020331444, ISSN: 0031-9155, DOI: 10.1088/1361-6560/AAE511.

* cited by examiner

SSIM=0.910

TRAINED MODEL GENERATION PROGRAM, IMAGE GENERATION PROGRAM, TRAINED MODEL GENERATION DEVICE, IMAGE GENERATION DEVICE, TRAINED MODEL GENERATION METHOD, AND IMAGE GENERATION METHOD

CROSS-REFERENCE TO RELATED APPLICATIONS

The present application is based on PCT filing PCT/JP2021/006833, filed Feb. 24, 2021, which claims priority to Japanese Patent Applications No. 2020-042154, filed on Mar. 11, 2020, the entire contents of each are incorporated herein by reference.

TECHNICAL FIELD

The present invention relates to a trained model generation program, an image generation program, a trained model generation device, an image generation device, a trained model generation method, and an image generation method.

BACKGROUND ART

For example, X-ray computed tomography (CT) devices that perform sparse-view CT which scans a subject with a reduced number of projection directions or low-dose CT which scans a subject with a limited electric current flowing through an X-ray tube have been used to reduce dose exposure of subjects. A reconstruction method using compressed sensing has been used as a primary reconstruction method to generate a high quality reconstructed image when such a scan is performed. This reconstruction method generates a reconstructed image using a model in which density changes of a reconstructed image are piecewise constant. Of such reconstruction methods, a reconstruction method called total variation (TV) is often used in medical X-ray CT devices.

Examples of such technology include a medical imaging device disclosed in Patent Document 1. This medical imaging device includes an image reconstruction unit that repeatedly performs optimization calculations for compressed sensing to reconstruct an image and a basis selection unit that selects a basis transformation to be used for optimization in each iteration. The basis selection unit selects a basis in a predetermined order of bases. Alternatively, the basis selection unit selects a basis using weighting coefficients preset for the basis.

CITATION LIST

Patent Document

Patent Document 1: JP 2018-134199 A

SUMMARY OF INVENTION

Technical Problem

However, because the medical imaging device described above employs compressed sensing, for example, stair-step artifacts, elimination of smooth density changes, elimination of textures, or things like that occur in a reconstructed image when sparse-view CT or low-dose CT is performed. Such image quality deteriorations are known to be conspicuous depending on the measurement conditions of sparse-view CT or low-dose CT.

The present invention has been made in view of the above circumstances and it is an object of the present invention to provide a trained model generation program, an image generation program, a trained model generation device, an image generation device, a trained model generation method, and an image generation method capable of mitigating image quality degradations occurring in a reconstructed image generated by a reconstruction method that uses compressed sensing.

Solution to Problem

An aspect of the present invention is a trained model generation program causing a computer to implement a learning execution function of inputting to a machine learning device first input image data representing a first input image generated by a first reconstruction method using compressed sensing and second input image data representing a second input image generated by a second reconstruction method different from the first reconstruction method, the second reconstruction method being an analytical reconstruction method, and causing the machine learning device to perform machine learning and generate a trained model, and a trained model acquisition function of acquiring trained model data indicating the trained model.

According to an aspect of the present invention, in the trained model generation program, the learning execution function may search for a smoothing parameter of the first reconstruction method, a weight used in a convolutional neural network that is used as the trained model, and a bias used in the convolutional neural network which minimize a mean squared error represented by the following equation (1) and cause the machine learning device to generate the trained model.

[Math. 1]

$$MSE(w, b, \beta) = \frac{1}{N}\sum_{i=1}^{N}\left\|x_i - CNN(w, b)\begin{bmatrix} y_i \\ z_i(\beta) \end{bmatrix}\right\|^2 \quad (1)$$

where w is a vector in which weights used in the convolutional neural network are arranged in a row, b is a vector in which biases used in the convolutional neural network are arranged in a row, β is a smoothing parameter of the first reconstruction method, $x_i$ is a vector in which values indicating densities represented by pixels of an output image are arranged in a row, $y_i$ is a vector in which values indicating densities represented by pixels of the second input image are arranged in a row, and $z_i$ is a vector in which values indicating densities represented by pixels of the first input image are arranged in a row.

According to an aspect of the present invention, in the trained model generation program, the learning execution function may input at least the first input image data representing the first input image generated by the first reconstruction method using the compressed sensing in which a first smoothing parameter is set and the first input image data representing the first input image generated by the first reconstruction method using the compressed sensing in which a second smoothing parameter with a different value from that of the first smoothing parameter is set to the machine learning device and cause the machine learning device to perform machine learning and generate the trained model.

According to an aspect of the present invention, in the trained model generation program, the learning execution function may input output image data representing an output image generated by a third reconstruction method different from the first reconstruction method, in addition to the first input image data, to the machine learning device and cause the machine learning device to perform machine learning and generate the trained model.

An aspect of the present invention is an image generation program causing a computer to implement an image generation function of inputting input image data representing an input image to the trained model generated by any of the above trained model generation programs to generate a reconstructed image.

An aspect of the present invention is a trained model generation device including a learning execution unit configured to input first input image data representing a first input image generated by a first reconstruction method using compressed sensing and second input image data representing a second input image generated by a second reconstruction method different from the first reconstruction method, the second reconstruction method being an analytical reconstruction method, to a machine learning device and cause the machine learning device to perform machine learning and generate a trained model and a trained model acquisition unit configured to acquire trained model data indicating the trained model.

An aspect of the present invention is an image generation device including an image generation unit configured to input input image data representing an input image to the trained model generated by the trained model generation device to generate a reconstructed image.

An aspect of the present invention is a trained model generation method including a learning execution step of inputting first input image data representing a first input image generated by a first reconstruction method using compressed sensing and second input image data representing a second input image generated by a second reconstruction method different from the first reconstruction method, the second reconstruction method being an analytical reconstruction method, to a machine learning device and causing the machine learning device to perform machine learning and generate a trained model and a trained model acquisition step of acquiring trained model data indicating the trained model.

An aspect of the present invention is an image generation method including an image generation step of inputting input image data representing an input image to the trained model generated by the trained model generation method to generate a reconstructed image.

Advantageous Effects of Invention

According to the present invention, it is possible to mitigate image quality degradations occurring in a reconstructed image generated by a reconstruction method that uses compressed sensing.

DESCRIPTION OF EMBODIMENTS

Embodiments

Figure 1:
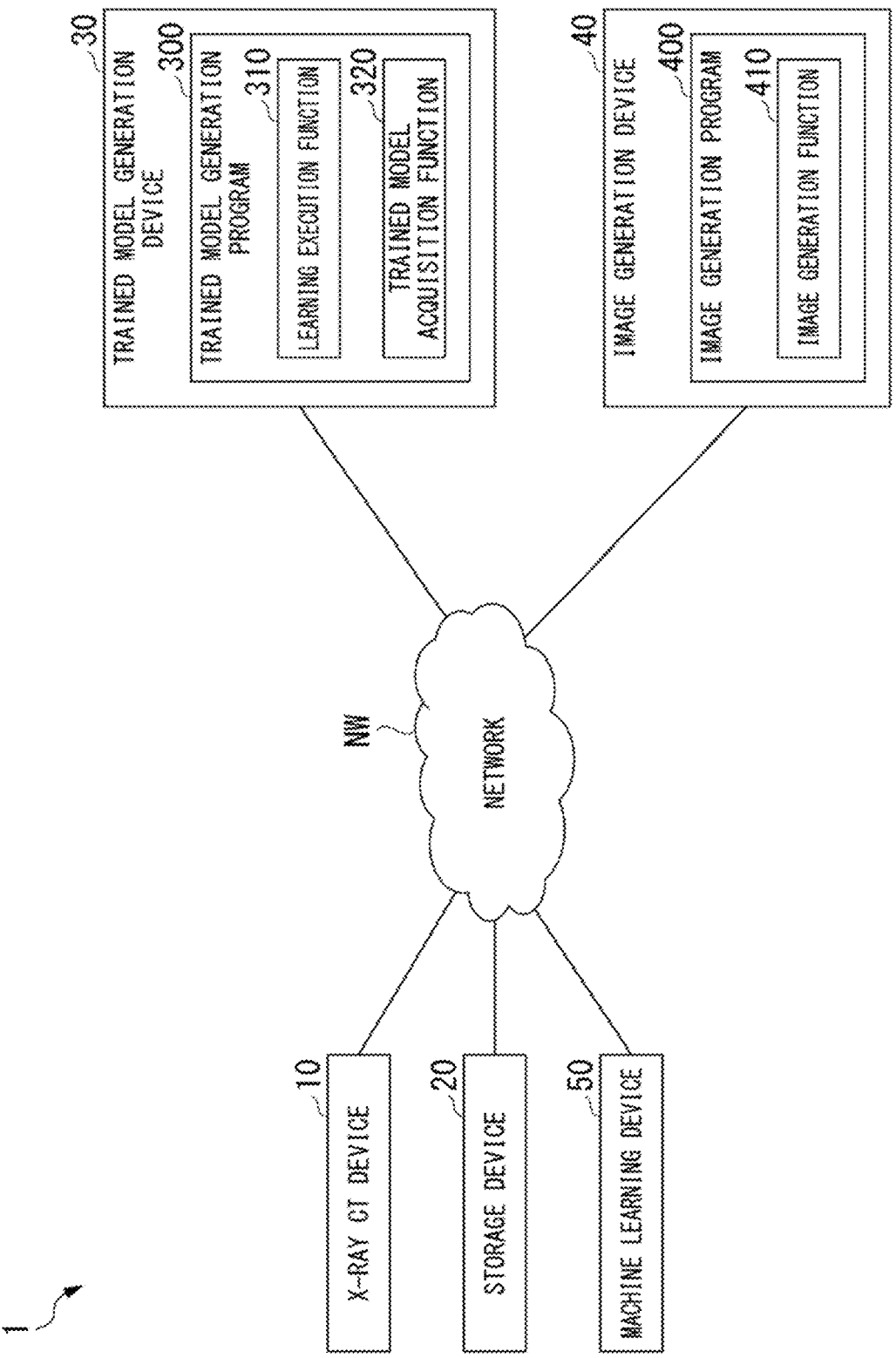
FIG. 1 is a diagram illustrating an example of an image generation system according to an embodiment.

Embodiments of the present invention will be described with reference to the drawings. FIG. 1 is a diagram illustrating an example of an image generation system according to an embodiment. As illustrated in FIG. 1, the image generation system 1 includes an X-ray CT device 10, a storage device 20, a trained model generation device 30, an image generation device 40, and a machine learning device 50. The X-ray CT device 10, the storage device 20, the trained model generation device 30, the image generation device 40, and the machine learning device 50 are all connected to a network NW. The network NW is, for example, the Internet, an intranet, a wide area network (WAN), or a local area network (LAN).

Figure 2:
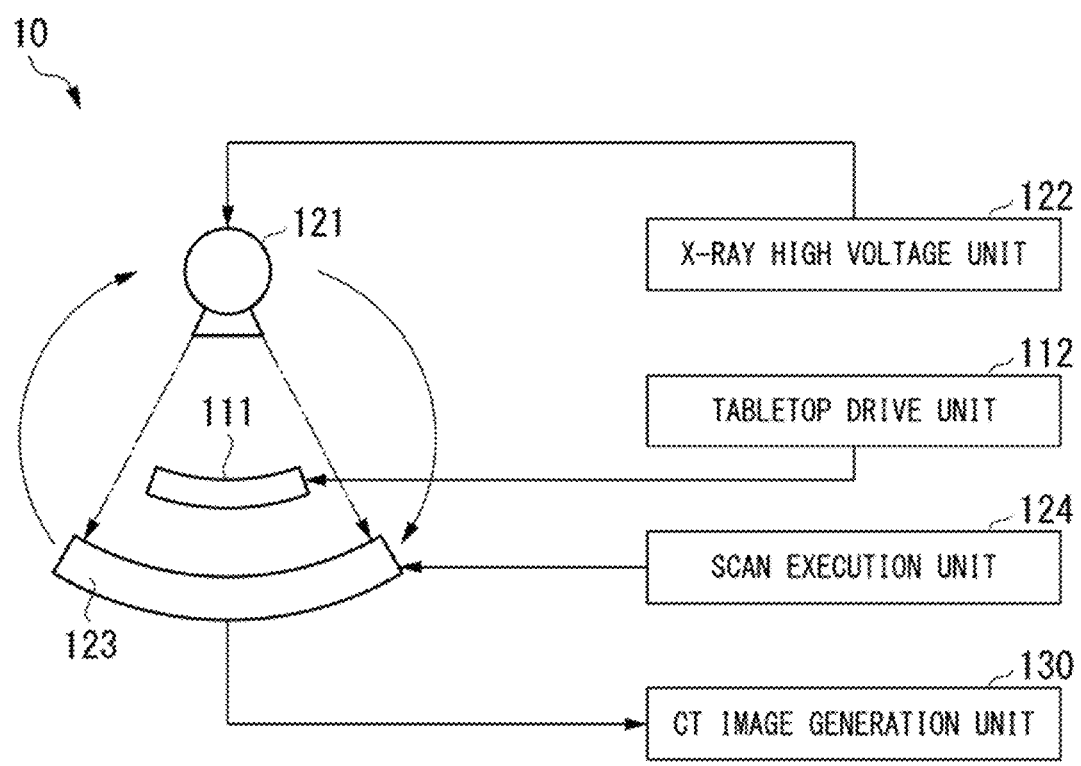
FIG. 2 is a diagram illustrating an example of an X-ray CT device according to the embodiment.

FIG. 2 is a diagram illustrating an example of the X-ray CT device according to the embodiment. As illustrated in FIG. 2, the X-ray CT device 10 includes a tabletop 111, a tabletop drive unit 112, an X-ray tube 121, an X-ray high voltage unit 122, an X-ray detector 123, a scan execution unit 124 and a CT image generation unit 130.

The tabletop 111 is a plate-like member on which a subject is placed. The tabletop drive unit 112 moves the tabletop 111 with respect to the X-ray tube 121 and the X-ray detector 123. The X-ray tube 121 generates X-rays with which the subject is irradiated. The X-ray high voltage unit 122 applies a high voltage to the X-ray tube 121. The X-ray detector 123 includes detection elements that detect X-rays emitted from the X-ray tube 121.

The scan execution unit 124 controls the tabletop drive unit 112, the X-ray tube 121, the X-ray high voltage unit 122, and the X-ray detector 123 to scan the subject and acquires a plurality of pieces of projection data. When the subject is scanned, the X-ray tube 121 and the X-ray detector 123 rotate around the subject while facing each other. The position of the X-ray tube 121 when each of the plurality of pieces of projection data is acquired is called a view. The CT image generation unit 130 generates a CT image by reconstructing the plurality of pieces of projection data generated by scanning the subject and stores CT image data representing the CT image in the storage device 20.

The X-ray CT device 10 can perform not only normal CT imaging but also sparse-view CT imaging which scans the subject with a reduced number of projection directions and low-dose CT imaging which scans the subject with a limited electric current flowing through the X-ray tube.

Each of the trained model generation device 30 and the image generation device 40 illustrated in FIG. 1 is, for example, a computer having a storage medium and a hardware processor.

The storage medium is, for example, a hard disk drive (HDD), a solid state drive (SSD), a flash memory, or a read only memory (ROM). The storage medium included in the trained model generation device 30 stores a trained model generation program 300 illustrated in FIG. 1. The storage medium included in the image generation device 40 stores an image generation program 400 illustrated in FIG. 1.

A hardware processor is, for example, a central processing unit (CPU). The hardware processor included in the trained model generation device 30 loads and executes the trained model generation program 300 to implement a learning execution function 310 and a trained model acquisition function 320 illustrated in FIG. 1. The hardware processor included in the image generation device 40 loads and executes the image generation program 400 to store an image generation function 410 illustrated in FIG. 1. The trained model generation program 300 and the image generation program 400 perform first processing, second processing, or third processing which will be described below.

First Processing

The learning execution function 310 inputs to the machine learning device 50 sets, each of which includes first input image data and output image data, and causes the machine learning device 50 to perform machine learning and generate a trained model. A piece of first input image data is a piece of data representing a first input image generated by a first reconstruction method using compressed sensing. A piece of output image data is a piece of data representing an output image that corresponds to the first input image, has less deterioration in image quality than the first input image, and is a correct answer for machine learning performed by the machine learning device 50. Specifically, the output image is generated by a third reconstruction method different from the first reconstruction method. Conditions in which the output image is generated are those with a normal dose and a normal number of projection directions.

In this case, one-to-one relationship or many-to-one relationship may exist between an entirety of first input images and an entirety of output images, one-to-one relationship or many-to-one relationship may exist between some of the first input images and some of the output images, or no relationship may exist between the first input images and the output images. Also, the number of first input images may or may not be equal to the number of output images.

Compressed sensing used in the first reconstruction method is, for example, total variation. The process of generating a first input image using total variation is a process of searching for a vector z which minimizes a value represented by the following equation (2) including a vector p, a matrix A, a vector z, and a smoothing parameter $\beta$ of the first reconstruction method. The vector p is a vector in which values indicating the intensities of X-rays represented by pixels of projection data acquired in each view are arranged in a row. The matrix A is a matrix whose elements represent the lengths of X-rays passing through minute areas included in a scanned area. The vector z is a vector in which values indicating densities represented by pixels of the first input image are arranged in a row. The smoothing parameter $\beta$ of the first reconstruction method is a parameter indicating a strength with which the first input image is smoothed. $\|z\|_{TV}$ is a total variation norm of the vector z.

[Math. 2]

$$\underset{z}{\text{minimize}} \; \|p - Az\|^2 + \beta \|z\|_{TV} \tag{2}$$

The first input image is a CT image generated by first-reconstructing projection data that the X-ray CT device 10 has generated by performing normal CT imaging, sparse-view CT imaging, or low-dose CT imaging. Alternatively, the first input image is a CT image generated by first-reconstructing projection data generated by another X-ray CT device.

Figure 3:
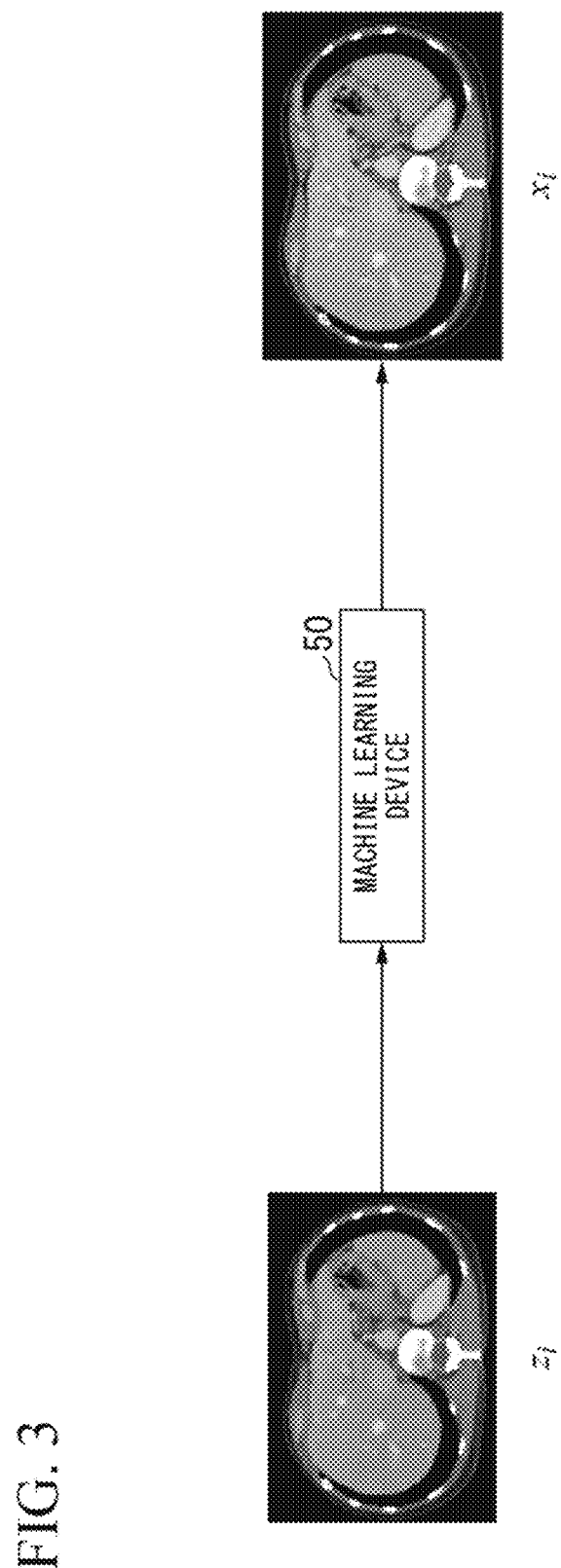
FIG. 3 is a diagram illustrating an example of machine learning performed by a machine learning device according to the embodiment.

The machine learning device 50 generates a trained model, for example, using a convolutional neural network (CNN). FIG. 3 is a diagram illustrating an example of machine learning performed by the machine learning device according to the embodiment. As illustrated in FIG. 3, the machine learning device 50 receives inputs of a vector $z_i$ regarding a piece of first input image data and a vector $x_i$ regarding a piece of output image data and performs machine learning. The process of performing machine learning and generating a trained model is a process of searching for a vector w, a vector b, and a smoothing parameter β of the first reconstruction method which minimize a mean squared error (MSE) represented by the following equation (3) including the number of samples N of sets of a first input image and an output image corresponding to the first input image used for machine learning, the vector w, the vector b, the smoothing parameter β of the first reconstruction method, the vector $x_i$, and the vector $z_i$. The vector w is a vector in which weights used in the convolutional neural network described above are arranged in a row. The vector b is a vector in which biases used in the convolutional neural network described above are arranged in a row. The vector $x_i$ is a vector in which values indicating densities represented by pixels of the output image are arranged in a row. The vector $z_i$ is a vector in which values indicating densities represented by pixels of the first input image are arranged in a row. Here, the smoothing parameter β of the first reconstruction method is the same as that described above. "CNN" included in equation (3) represents the convolutional neural network.

[Math. 3]

$$MSE(w, b, \beta) = \frac{1}{N}\sum_{i=1}^{N}\|x_i - CNN(w, b)z_i(\beta)\|^2 \quad (3)$$

The trained model acquisition function 320 acquires trained model data indicating a trained model. Then, the trained model acquisition function 320 causes the storage device 20 to store the trained model data.

The image generation function 410 inputs a piece of input image data to the trained model indicated by the trained model data stored in the storage device 20 to generate a reconstructed image. A piece of input image data is a piece of data representing an input image. The input image is an image generated by the same compressed sensing as that for the first input image used for learning described above.

The process by which the image generation function 410 generates a reconstructed image is represented by the following equation (4) including a vector x, the vector w, the vector b, a vector z, and the smoothing parameter β of the first reconstruction method. Here, the vector w, the vector b, the vector z, and the smoothing parameter β of the first reconstruction method are all the same as those described above. "CNN" included in equation (4) represents the convolutional neural network. The vector w, the vector b, and the smoothing parameter β of the first reconstruction method are automatically determined in the learning process for generating the trained model.

[Math. 4]

$$X = CNN(w,b)z(\beta) \quad (4)$$

Second Processing

The learning execution function 310 inputs sets, each including first input image data, second input image data, and output image data, to the machine learning device 50 and causes the machine learning device 50 to perform machine learning and generate a trained model. A piece of first input image data and the piece of output image data are the same as those of the first processing described above.

In this case, the plurality of first input images, the plurality of second input images, and the plurality of output images may all be in one-to-one correspondence, may all be in many-to-one correspondence, only some may be in one-to-one correspondence, only some may be in many-to-one correspondence, or they may not have any correspondence. Also, the number of first input images, the number of second input images, and the number of output images may or may not match.

In this case, the plurality of first input images and the plurality of second input images may all be in one-to-one correspondence, may all be in many-to-one correspondence, only some may be in one-to-one correspondence, only some may be in many-to-one correspondence, or they may not have any correspondence. Also, the number of first input images and the number of second input images may or may not match. The same is true for the relationship between first input images and output images and for the relationship between second input images and output images.

A piece of second input image data is a piece of data representing a second input image generated by a second reconstruction method that is an analytical reconstruction method. The second reconstruction method is, for example, filtered back-projection (FBP). The second input image is a CT image generated by second-reconstructing projection data that the X-ray CT device 10 has generated by performing normal CT imaging, sparse-view CT imaging, or low-dose CT imaging. Alternatively, the second input image is a CT image generated by second-reconstructing projection data generated by another X-ray CT device.

Figure 4:
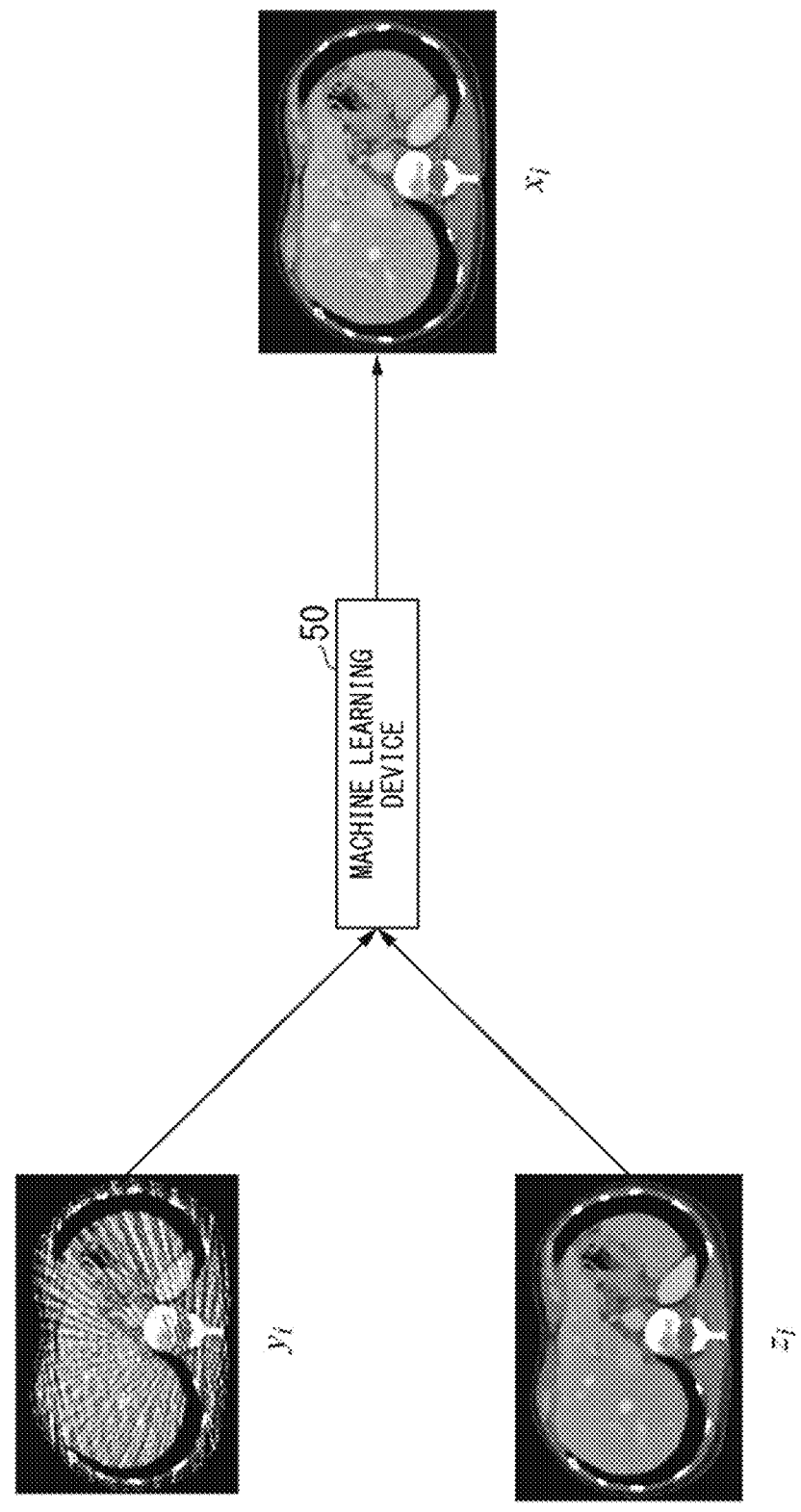
FIG. 4 is a diagram illustrating an example of machine learning executed by the machine learning device according to the embodiment.

The machine learning device 50 generates a trained model, for example, using a convolutional neural network. FIG. 4 is a diagram illustrating an example of machine learning performed by the machine learning device according to the embodiment. As illustrated in FIG. 4, the machine learning device 50 receives inputs of a vector $z_i$ regarding a piece of first input image data, a vector $y_i$ regarding a piece of second input image data, and a vector $x_i$ regarding a piece of output image data and performs machine learning. The process of performing machine learning and generating a trained model is a process of searching for a vector w, a vector b, and a smoothing parameter β of the first reconstruction method which minimize a mean squared error represented by the following equation (5) including the number of samples N of sets of a first input image, a second input image, and an output image, the vector w, the vector b, the smoothing parameter β of the first reconstruction method, the vector $x_i$, the vector $y_i$, and the vector $z_i$. The vector $y_i$ is a vector in which values indicating densities represented by pixels of the second input image are arranged in a row. Here, the vector w, the vector b, the smoothing parameter β of the first reconstruction method, the vector $x_i$, and the vector $z_i$ are the same as those of the first processing.

[Math. 5]

$$MSE(w, b, \beta) = \frac{1}{N} \sum_{i=1}^{N} \left\| x_i - CNN(w, b) \begin{bmatrix} y_i \\ z_i(\beta) \end{bmatrix} \right\|^2 \quad (5)$$

The trained model acquisition function 320 acquires trained model data indicating a trained model. Then, the trained model acquisition function 320 causes the storage device 20 to store the trained model data.

The image generation function 410 inputs a piece of input image data to the trained model indicated by the trained model data stored in the storage device 20 to generate a reconstructed image. A piece of input image data is a piece of data representing an input image. The input image is, for example, an image generated by the same compressed sensing as that for the first input image described above or by the same analytical reconstruction method as that for the second input image described above.

The process by which the image generation function 410 generates a reconstructed image is represented by the following equation (6) including a vector x, the vector w, the vector b, a vector y, a vector z, and the smoothing parameter $\beta$ of the first reconstruction method. The vector y is a vector in which values indicating densities represented by pixels of the second input image are arranged in a row. Here, the vector x, the vector w, the vector b, the vector z, and the smoothing parameter $\beta$ of the first reconstruction method are all the same as those of the first processing. "CNN" included in equation (6) represents a convolutional neural network.

[Math. 6]

$$x = CNN(w, b) \begin{bmatrix} y \\ z(\beta) \end{bmatrix} \quad (6)$$

Third Processing

The learning execution function 310 inputs to the machine learning device 50 sets, each of which includes at least two types of first input image data individually generated by the first reconstruction method configured with a smoothing parameter different from each other and output image data, and causes the machine learning device 50 to perform machine learning and generate a trained model. A first type of first input image data is a piece of data representing a first input image generated by the first reconstruction method using compressed sensing in which a first smoothing parameter is set. A second type of first input image data is a piece of data representing a first input image generated by the first reconstruction method using compressed sensing in which a second smoothing parameter with a different value from that of the first smoothing parameter is set.

Similarly, the learning execution function 310 may input to the machine learning device 50 sets, each of which includes not only the first and second types of first input image data but also the third to M-th types (where M is a natural number of 3 or more) of first input image data, and causes the machine learning device 50 to perform machine learning and generate a trained model. In this case, the learning execution function 310 inputs to the machine learning device 50 sets, each of which includes three or more types of first input image data, and causes the machine learning device 50 to perform machine learning and generate a trained model. A M-th type of first input image data is a piece of data representing a first input image generated by the first reconstruction method using compressed sensing in which an M-th smoothing parameter with a different value from those of the other smoothing parameters is set.

That is, the learning execution function 310 inputs to the machine learning device 50 sets, each of which includes a plurality of first input images individually generated by the first reconstruction method using compressed sensing configured with a smoothing parameter different from each other and an output image, and causes the machine learning device 50 to perform machine learning and generate a trained model.

In this case, one-to-one relationship or many-to-one relationship may exist between a first input image group including a plurality of types of first input images and an entirety of output images, one-to-one relationship or many-to-one relationship may exist between some of the first input image group and some of the output images, or no relationship may exist between the first input image group and the output images. Also, the number of first input image groups may or may not be equal to the number of output images.

Figure 5:
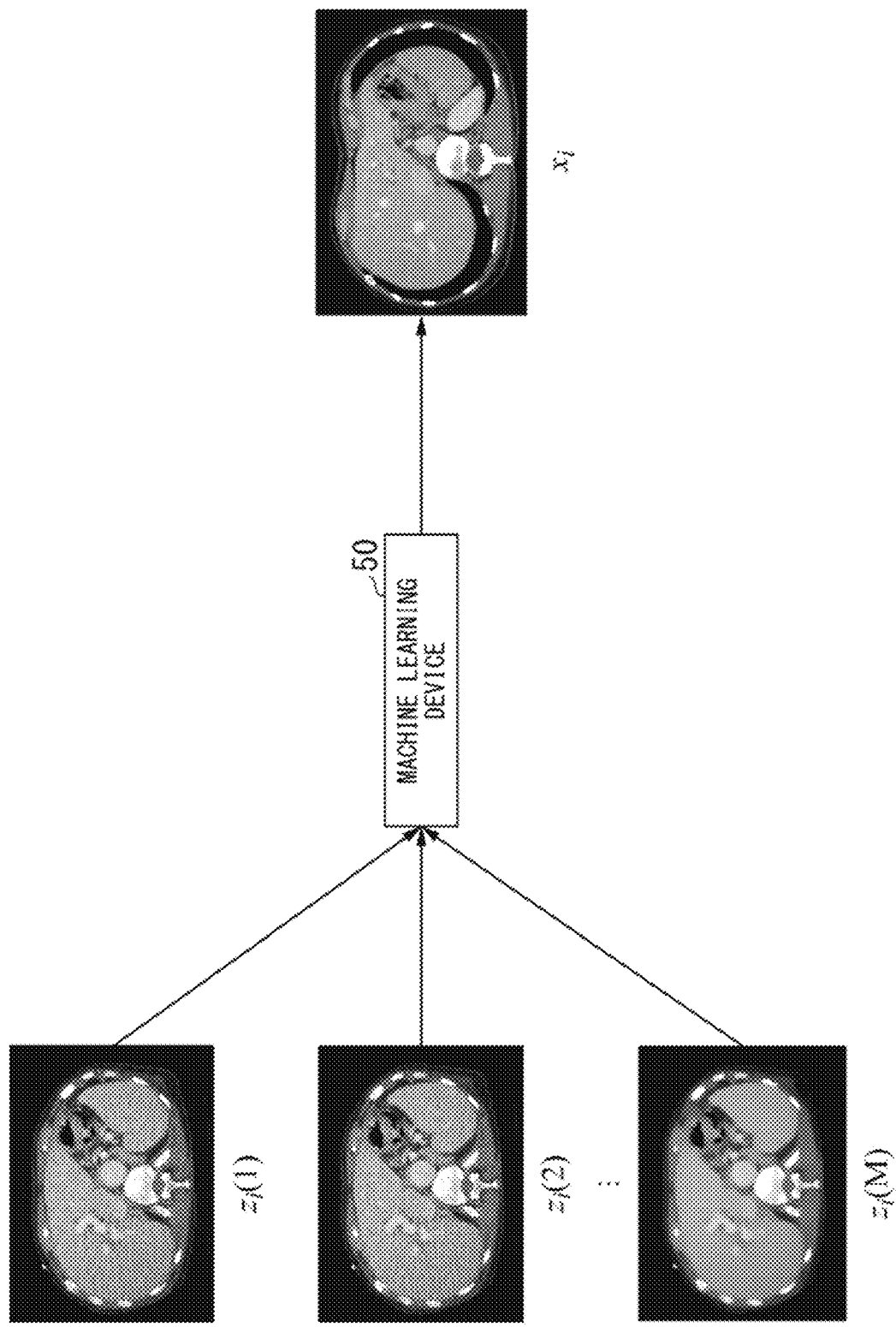
FIG. 5 is a diagram illustrating an example of machine learning executed by the machine learning device according to the embodiment.

The machine learning device 50 generates a trained model, for example, using a convolutional neural network. FIG. 5 is a diagram illustrating an example of machine learning performed by the machine learning device according to the embodiment. As illustrated in FIG. 5, the machine learning device 50 receives inputs of a vector $z_i(1)$, a vector $z_i(2)$, . . . , and a vector $z_i(M)$ regarding a plurality of pieces of first input image data and a vector $x_i$ regarding a piece of output image data and performs machine learning. The process of performing machine learning and generating a trained model is a process of searching for a vector w and a vector b which minimize a mean squared error represented by the following equation (7) including the number of samples N of sets of first input images and a corresponding output image used for learning, the vector w, the vector b, the vector $x_i$, the vector $z_i(1)$, the vector $z_i(2)$, . . . , and the vector $z_i(M)$ (where M is a natural number of 2 or more). The vector $z_i(1)$, the vector $z_i(2)$, . . . , and the vector $z_i(M)$ are each a vector in which values indicating densities represented by pixels of a first input image are arranged in a row. Here, the vector w, the vector b, and the vector $x_i$ are the same as those of the first processing.

[Math. 7]

$$MSE(w, b) = \frac{1}{N} \sum_{i=1}^{N} \left\| x_i - CNN(w, b) \begin{bmatrix} z_i(1) \\ z_i(2) \\ \vdots \\ z_i(M) \end{bmatrix} \right\|^2 \quad (7)$$

The trained model acquisition function 320 acquires trained model data indicating a trained model. Then, the trained model acquisition function 320 causes the storage device 20 to store the trained model data.

The image generation function 410 inputs pieces of input image data to the trained model indicated by the trained model data stored in the storage device 20 to generate a reconstructed image. The pieces of input image data are a vector $z_i(1)$, a vector $z_i(2)$, . . . , and a vector $z_i(M')$ indicating M' input images (where M' is a natural number of 2 or more). The input images are images generated by the same method as the plurality of types of first input images described above, that is, images generated by compressed sensing in which different smoothing parameters are set. Here, M' may be equal to or different from M described above.

The process by which the image generation function 410 generates a reconstructed image is represented by the following equation (8) including a vector x, the vector w, the vector b, a vector z(1), a vector z(2), ..., and a vector z(M). The vector z(1), the vector z(2), ..., and the vector z(M) are each a vector in which values indicating densities represented by pixels of a first input image are arranged in a row. Here, the vector x, the vector w, and the vector b are all the same as those of the first processing. "CNN" included in equation (8) represents the convolutional neural network.

[Math. 8]

$$x = CNN(w, b) \begin{bmatrix} z(1) \\ z(2) \\ \vdots \\ z(M) \end{bmatrix} \quad (8)$$

Figure 6:
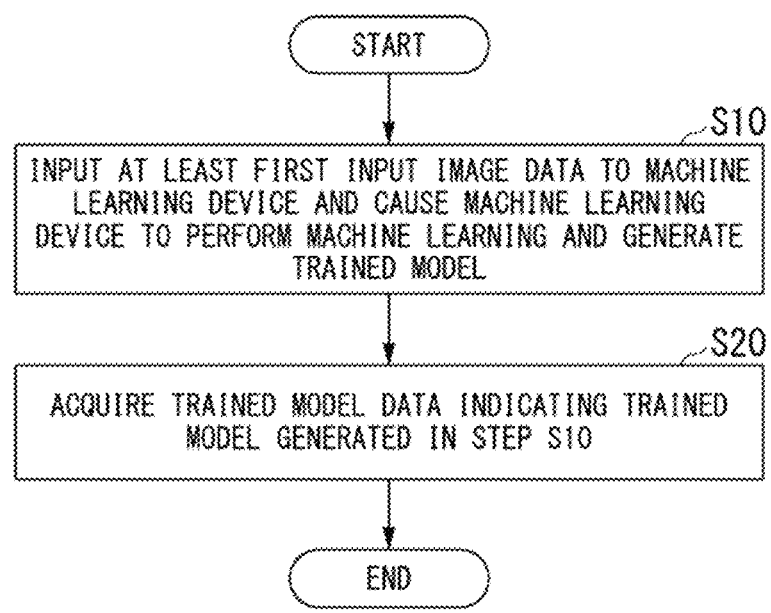
FIG. 6 is a flowchart showing an example of a process performed by a trained model generation program according to the embodiment.

Next, an example of a process executed by the trained model generation program 300 according to the embodiment will be described with reference to FIG. 6. FIG. 6 is a flowchart showing an example of a process performed by the trained model generation program according to the embodiment.

In step S10, the learning execution function 310 inputs at least first input image data to the machine learning device 50 and causes the machine learning device 50 to perform machine learning and generate a trained model.

In step S20, the trained model acquisition function 320 acquires trained model data indicating the trained model generated in step S10.

The trained model generation program 300 and the image generation program 400 according to the embodiment have been described above.

The trained model generation program 300 inputs first input image data representing a first input image generated by a first reconstruction method that uses compressed sensing to the machine learning device 50 and causes the machine learning device 50 to perform machine learning and generate a trained model. Then, the trained model generation program 300 acquires trained model data indicating the trained model.

Thus, the trained model generation program 300 can generate a trained model that can generate a reconstructed image that mitigates stair-step artifacts, elimination of smooth density changes, elimination of textures, and things like that occur in the first input image due to compressed sensing. The trained model generation program 300 can achieve this effect simply by inputting first input image data to the machine learning device 50 even when a desirable value of the smoothing parameter β of the first reconstruction method is unknown.

The trained model generation program 300 inputs second input image data representing a second input image generated by a second reconstruction method different from the first reconstruction method, the second reconstruction method being an analytical reconstruction method, in addition to the first input image data, to the machine learning device 50 and causes the machine learning device 50 to perform machine learning and generate a trained model. The analytical reconstruction method has an advantage of being able to generate a reconstructed image that reproduces smooth density changes with relatively high accuracy.

Thus, the trained model generation program 300 can generate a trained model that can, with the above advantage, compensate for stair-step artifacts, elimination of smooth density changes, elimination of textures, and things like that occur in the first input image due to compressed sensing. The trained model generation program 300 can achieve this effect simply by inputting first input image data and second input image data to the machine learning device 50 even when a desirable value of the smoothing parameter β of the first reconstruction method is unknown.

The trained model generation program 300 searches for a smoothing parameter β of the first reconstruction method, weights w used in a convolutional neural network that is used as the trained model, and biases b used in the convolutional neural network which minimize a mean squared error represented by the above equation (5) to cause the machine learning device 50 to generate the trained model.

Thus, because the trained model generation program 300 generates the trained model by searching for a desirable value for the smoothing parameter β of the first reconstruction method in the process of learning, the trained model generation program 300 can save a person who intends to cause the image generation program 400 to generate a reconstructed image with the effort of determining a specific value of the smoothing parameter β of the first reconstruction method through trial and error. This effect is particularly effective because it is often difficult to empirically determine a desirable value for the smoothing parameter β of the first reconstruction method.

The trained model generation program 300 inputs at least two types of first input image data generated by a first reconstruction method in which different smoothing parameters are set to the machine learning device 50 and causes the machine learning device 50 to perform machine learning and generate a trained model.

Thus, the trained model generation program 300 can incorporate features of a plurality of reconstructed images with different smoothing strengths, thereby generating a trained model that can generate a reconstructed image that mitigates stair-step artifacts, elimination of smooth density changes, elimination of textures, and things like that occur in the first input image due to compressed sensing. The trained model generation program 300 can achieve this effect simply by inputting at least two types of first input image data to the machine learning device 50 even when a desirable value of the smoothing parameter β of the first reconstruction method is unknown.

The trained model generation program 300 inputs output image data representing an output image generated under conditions of a normal dose and a normal number of projection directions, in addition to the first input image data, to the machine learning device 50 and causes the machine learning device 50 to perform machine learning and generate a trained model.

Thus, the trained model generation program 300 can cause the machine learning device 50 to perform supervised learning and generate a trained model with higher accuracy.

The image generation program 400 inputs input image data representing an input image to the trained model generated by the trained model generation program 300 to generate a reconstructed image.

Thus, the image generation program 400 can mitigate image quality degradations occurring in a reconstructed image generated by a reconstruction method that uses compressed sensing.

Figure 7:
FIG. 7 is a diagram showing an example of a reconstructed image generated by reconstructing projection data acquired through a scan in which a normal dose and a normal number of projection data directions are set.

Next, a first specific example regarding the above effects will be described with reference to FIGS. 7 to 11. FIG. 7 is a diagram showing an example of a reconstructed image generated by reconstructing projection data acquired through a scan in which a normal dose and a normal number of projection data directions are set. The closer a reconstructed image is to a reconstructed image P7 shown in FIG. 7, the less it has deterioration in image quality due to compressed sensing.

Figure 8:
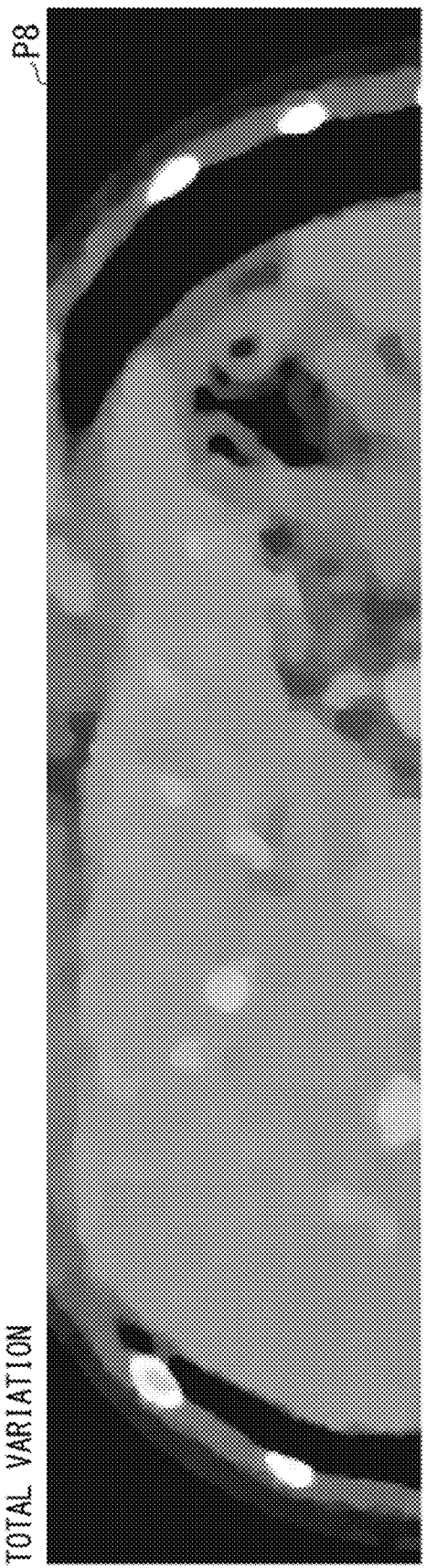
FIG. 8 is a diagram showing an example of a reconstructed image generated by reconstructing projection data acquired through sparse-view CT by a reconstruction method that uses total variation.

FIG. 8 is a diagram showing an example of a reconstructed image generated by reconstructing projection data acquired through sparse-view CT by a reconstruction method that uses total variation. A reconstructed image P8 shown in FIG. 8 is generated from projection data of 64 directions acquired by sparse-view CT imaging. As shown in the lower left of FIG. 8, the reconstructed image P8 has a mean squared error of 82.19 and an image evaluation index (a structural similarity (SSIM)) of 0.89.

Here, the mean squared error is calculated by the following equation (9) including a function g(i, j) representing the reconstructed image P7 of the normal dose and the normal number of projection directions, a function f(i, j) representing a target reconstructed image, and the total number of pixels L in each of the two reconstructed images. An index i and an index j are indices indicating the position of each pixel of the two reconstructed images.

[Math. 9]

$$MSE = \frac{1}{L}\sum_i\sum_j (g(i, j) - f(i, j))^2 \quad (9)$$

The image evaluation index is calculated by the following equation (10), which has a larger value as the reconstructed image is closer to the reconstructed image P7. Details of equation (10) are described in a posted paper "Z. Wang, A. C. Bovik, H. R. Sheikh and E. P. Simoncelli, "Image quality assessment: From error visibility to structural similarity," IEEE Transactions on Image Processing, vol. 13, no. 4, pp. 600-612, April 2004."

[Math. 10]

$$SSIM = \frac{(2\mu_g\mu_f + C_1)(2\sigma_{gf} + C_2)}{(\mu_g^2 + \mu_f^2 + C_1)(\sigma_g^2 + \sigma_g^2 + C_2)} \quad (10)$$

In the reconstructed image P8 shown in FIG. 8, relatively low contrast structures such as blood vessels are rendered in white to the same extent as in the reconstructed image P7 shown in FIG. 7. However, smooth density changes and fine textures rendered in the reconstructed image P7 are lost throughout the reconstructed image P8 because the reconstructed image P8 has been smoothed by total variation.

Figure 9:
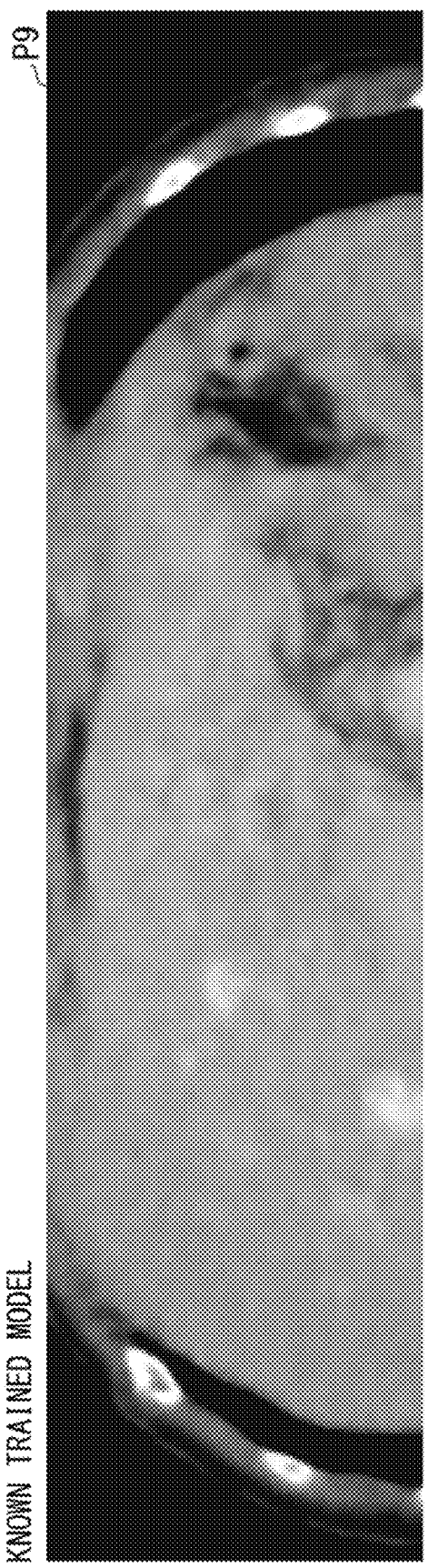
FIG. 9 is a diagram showing an example of a reconstructed image generated using a known trained model.

FIG. 9 is a diagram showing an example of a reconstructed image generated using a known trained model. The known trained model referred to here is a trained model generated by inputting only reconstructed images generated by the filtered back-projection method and output images generated under the conditions of the normal dose and the normal number of projection directions to a machine learning device that uses a convolution neural network and causing the machine learning device to perform learning. A reconstructed image P9 shown in FIG. 9 is generated from projection data of 64 directions acquired by sparse-view CT imaging. As shown in the lower left of FIG. 9, the reconstructed image P9 has a mean squared error of 79.06 and an image evaluation index of 0.88.

The reconstructed image P9 shown in FIG. 9 reproduces smooth density changes and fine textures rendered in the reconstructed image P7 shown in FIG. 7 to some or greater extent throughout. However, the reconstructed image P9 fails to render a part of the relatively low contrast structures rendered in white in the reconstructed image P7.

Figure 10:
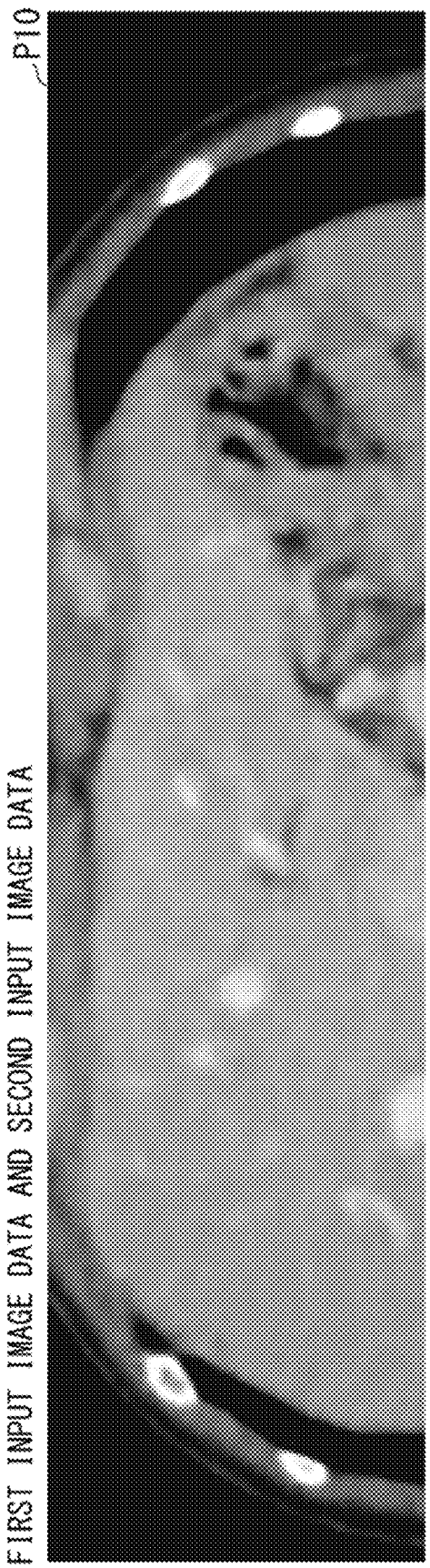
FIG. 10 is a diagram showing an example of a reconstructed image generated using a trained model generated by inputting first input image data and second input image data to the machine learning device according to the embodiment.

FIG. 10 is a diagram showing an example of a reconstructed image generated using a trained model generated by inputting first input image data and second input image data to a machine learning device according to the embodiment. A reconstructed image P10 shown in FIG. 10 is generated from projection data of 64 directions acquired by sparse-view CT imaging. As shown in the lower left of FIG. 10, the reconstructed image P10 has a mean squared error of 34.96 and an image evaluation index of 0.91.

The reconstructed image P10 shown in FIG. 10 reproduces smooth density changes and fine textures rendered in the reconstructed image P7 shown in FIG. 7 with high accuracy throughout. In the reconstructed image P10, relatively low contrast structures are rendered in white to the same extent as in the reconstructed image P7 shown in FIG. 7. In the reconstructed images shown in FIGS. 8 to 11, the reconstructed image P10 is closest to the reconstructed image shown in FIG. 7.

Figure 11:
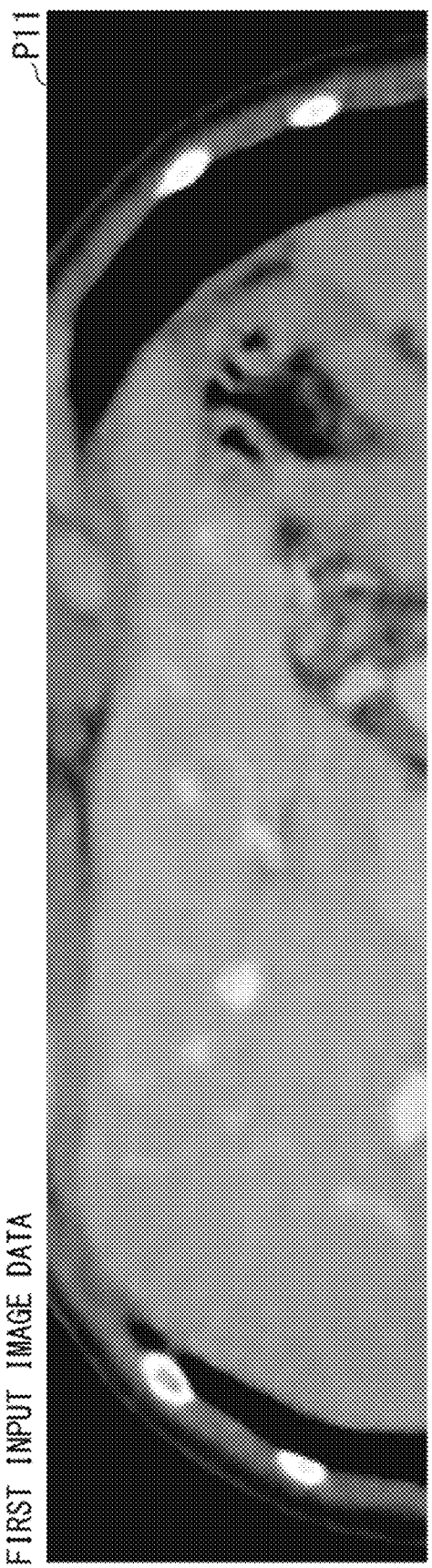
FIG. 11 is a diagram showing an example of a reconstructed image generated using a trained model generated by inputting first input image data to the machine learning device according to the embodiment.

FIG. 11 is a diagram showing an example of a reconstructed image generated using a trained model generated by inputting first input image data to a machine learning device according to the embodiment. A reconstructed image P11 shown in FIG. 11 is generated from projection data of 64 directions acquired by sparse-view CT imaging. As shown in the lower left of FIG. 11, the reconstructed image P11 has a mean squared error of 37.15 and an image evaluation index of 0.91.

The reconstructed image P11 shown in FIG. 11 reproduces smooth density changes and fine textures rendered in the reconstructed image P7 shown in FIG. 7 to some or greater extent throughout. In the reconstructed image P11, relatively low contrast structures are rendered in white to the same extent as in the reconstructed image P7 shown in FIG. 7. However, because the reconstructed image P11 does not incorporate an advantage of the analytical reconstruction method that it is possible to generate a reconstructed image that reproduces smooth density changes with relatively high accuracy, smooth density changes and fine textures rendered in the reconstructed image P7 are lost throughout the reconstructed image P11 more than in the reconstructed image P10 while the reconstructed image P11 is smoothed to some extent like the reconstructed image P8 shown in FIG. 8. In the reconstructed images shown in FIGS. 8 to 11, the reconstructed image P11 is second closest to the reconstructed image shown in FIG. 7.

Figure 12:
FIG. 12 is a diagram showing an example of a reconstructed image generated by reconstructing projection data acquired through a scan in which a normal dose and a normal number of projection data directions are set.

Next, a second specific example regarding the above effects will be described with reference to FIGS. 12 to 16. FIG. 12 is a diagram showing an example of a reconstructed image generated by reconstructing projection data acquired through a scan in which a normal dose and a normal number of projection data directions are set. The closer a reconstructed image is to a reconstructed image P12 shown in FIG. 12, the less it has deterioration in image quality.

Figure 13:
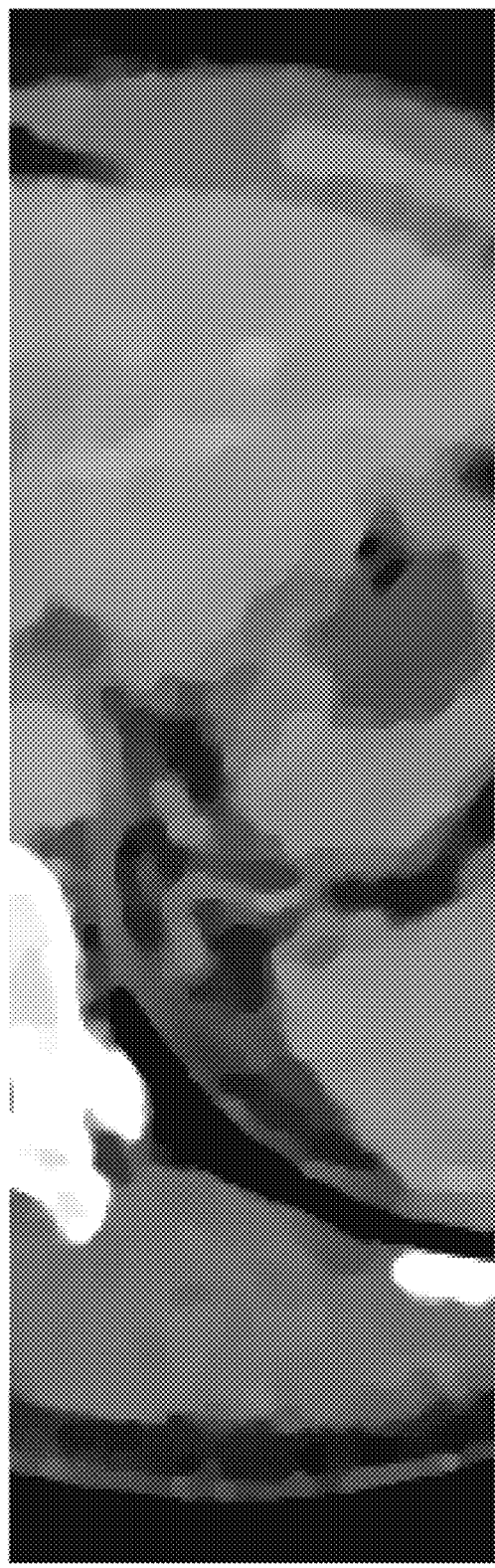
FIG. 13 is a diagram showing an example of a reconstructed image generated by reconstructing projection data acquired through sparse-view CT by a reconstruction method that uses total variation.

FIG. 13 is a diagram showing an example of a reconstructed image generated by reconstructing projection data acquired through sparse-view CT by a reconstruction method that uses total variation. A reconstructed image P13 shown in FIG. 13 is generated from projection data of 64 directions acquired by sparse-view CT imaging. As shown in the lower left of FIG. 13, the reconstructed image P13 has a mean squared error of 98.56 and an image evaluation index of 0.86.

In the reconstructed image P13 shown in FIG. 13, relatively low contrast structures such as blood vessels are rendered in light gray to the same extent as in the reconstructed image P12 shown in FIG. 12. However, smooth density changes and fine textures rendered in the reconstructed image P12 are lost throughout the reconstructed image P13 because the reconstructed image P13 has been smoothed by total variation.

Figure 14:
FIG. 14 is a diagram showing an example of a reconstructed image generated using a known trained model.

FIG. 14 is a diagram showing an example of a reconstructed image generated using a known trained model. A reconstructed image P14 shown in FIG. 14 is generated from projection data of 64 directions acquired by sparse-view CT imaging. As shown in the lower left of FIG. 14, the reconstructed image P14 has a mean squared error of 76.25 and an image evaluation index of 0.84.

The reconstructed image P14 shown in FIG. 14 reproduces smooth density changes and fine textures rendered in the reconstructed image P12 shown in FIG. 12 to some or greater extent throughout. However, the reconstructed image P14 fails to render a part of the relatively low contrast structures rendered in light gray in the reconstructed image P12.

Figure 15:
FIG. 15 is a diagram showing an example of a reconstructed image generated using a trained model generated by inputting first input image data and second input image data to the machine learning device according to the embodiment.

FIG. 15 is a diagram showing an example of a reconstructed image generated using a trained model generated by inputting first input image data and second input image data to a machine learning device according to the embodiment. A reconstructed image P15 shown in FIG. 15 is generated from projection data of 64 directions acquired by sparse-view CT imaging. As shown in the lower left of FIG. 15, the reconstructed image P15 has a mean squared error of 43.55 and an image evaluation index of 0.88.

The reconstructed image P15 shown in FIG. 15 reproduces smooth density changes and fine textures rendered in the reconstructed image P12 shown in FIG. 12 with high accuracy throughout. In the reconstructed image P15, relatively low contrast structures are rendered in light gray to the same extent as in the reconstructed image P12 shown in FIG. 12. In the reconstructed images shown in FIGS. 13 to 16, the reconstructed image P15 is closest to the reconstructed image shown in FIG. 12.

Figure 16:
FIG. 16 is a diagram showing an example of a reconstructed image generated using a trained model generated by inputting first input image data to the machine learning device according to the embodiment.

FIG. 16 is a diagram showing an example of a reconstructed image generated using a trained model generated by inputting first input image data to a machine learning device according to the embodiment. A reconstructed image P16 shown in FIG. 16 is generated from projection data of 64 directions acquired by sparse-view CT imaging. As shown in the lower left of FIG. 16, the reconstructed image P16 has a mean squared error of 59.01 and an image evaluation index of 0.87.

The reconstructed image P16 shown in FIG. 16 reproduces smooth density changes and fine textures rendered in the reconstructed image P12 shown in FIG. 12 to some or greater extent throughout. In the reconstructed image P16, relatively low contrast structures are rendered in light gray to the same extent as in the reconstructed image P12 shown in FIG. 12. However, because the reconstructed image P16 does not incorporate an advantage of the analytical reconstruction method that it is possible to generate a reconstructed image that reproduces smooth density changes with relatively high accuracy, smooth density changes and fine textures rendered in the reconstructed image P12 are lost throughout the reconstructed image P16 more than in the reconstructed image P15 while the reconstructed image P16 is somewhat smoothed like the reconstructed image P13 shown in FIG. 13. In the reconstructed images shown in FIGS. 13 to 16, the reconstructed image P16 is second closest to the reconstructed image shown in FIG. 12.

Figure 17:
FIG. 17 is a diagram showing an example of a reconstructed image generated by reconstructing projection data acquired through a scan in which a normal dose and a normal number of projection data directions are set.

Next, a third specific example regarding the above effects will be described with reference to FIGS. 17 to 21. FIG. 17 is a diagram showing an example of a reconstructed image generated by reconstructing projection data acquired through a scan in which a normal dose and a normal number of projection data directions are set. The closer a reconstructed image is to a reconstructed image P17 shown in FIG. 17, the less it has a deterioration in image quality.

Figure 18:
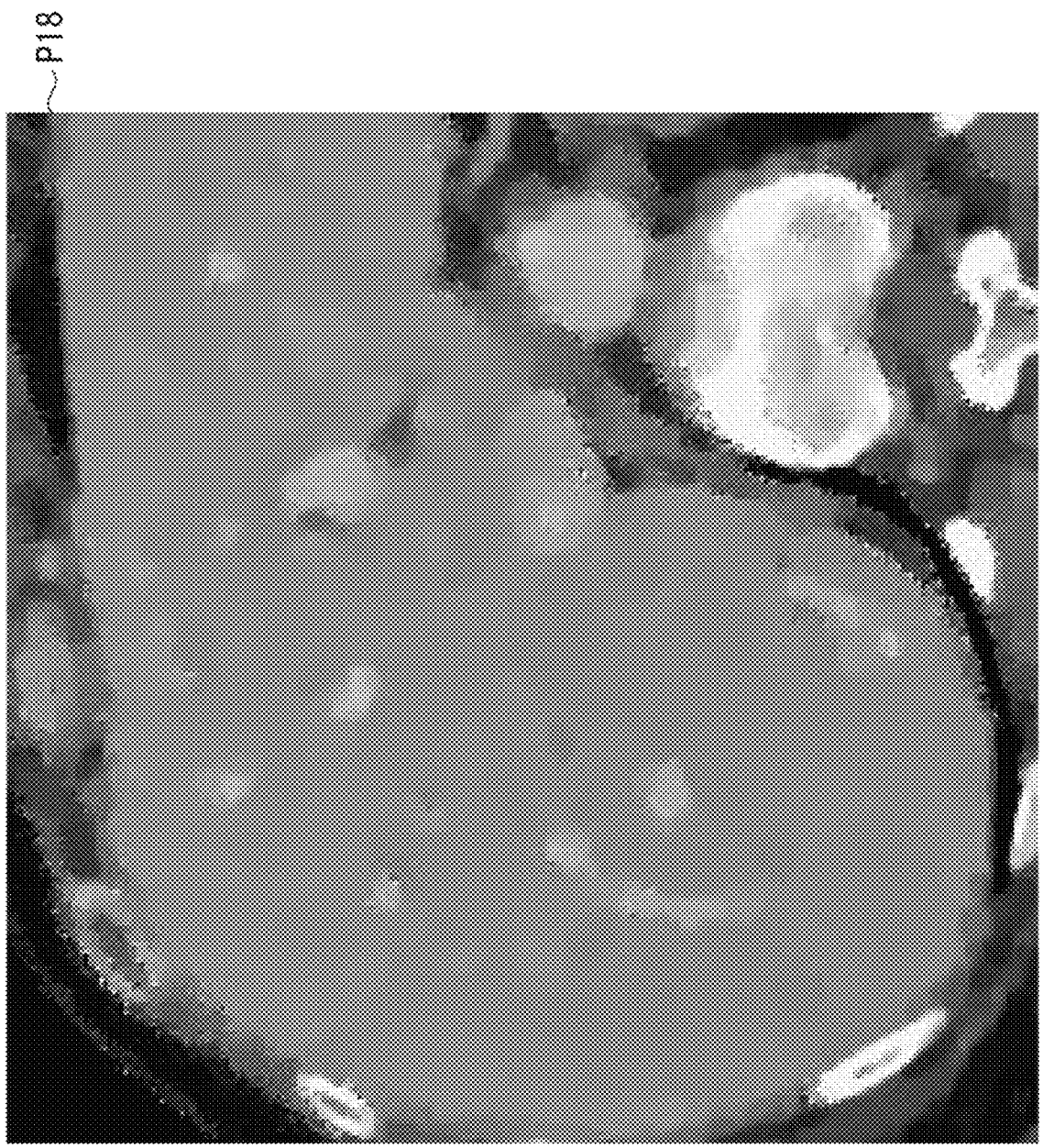
FIG. 18 is a diagram showing an example of a reconstructed image generated by reconstructing projection data acquired through sparse-view CT by a reconstruction method that uses total variation.

FIG. 18 is a diagram showing an example of a reconstructed image generated by reconstructing projection data acquired through sparse-view CT by a reconstruction method that uses total variation. A reconstructed image P18 shown in FIG. 18 is generated from projection data of 64 directions acquired by sparse-view CT imaging. As shown in the lower left of FIG. 18, the reconstructed image P18 has an image evaluation index of 0.586. This image evaluation index is generated for 100 cases using a trained model generated by the machine learning device 50 and is an average of the image evaluation indexes of reconstructed images that mainly render the liver. The same is true for image evaluation indexes shown in the lower left of FIGS. 19 to 21.

In the reconstructed image P18 shown in FIG. 18, relatively low contrast structures such as blood vessels are rendered in light gray to the same extent as in the reconstructed image P12 shown in FIG. 17. However, smooth density changes and fine textures rendered in the reconstructed image P17 are lost throughout the reconstructed image P18 because the reconstructed image P18 has been smoothed by total variation.

Figure 19:
FIG. 19 is a diagram showing an example of a reconstructed image generated using a known trained model.

FIG. 19 is a diagram showing an example of a reconstructed image generated using a known trained model. A reconstructed image P19 shown in FIG. 19 is generated from projection data of 64 directions acquired by sparse-view CT imaging. As shown in the lower left of FIG. 19, the reconstructed image P19 has an image evaluation index of 0.823.

The reconstructed image P19 shown in FIG. 19 reproduces smooth density changes and fine textures rendered in the reconstructed image P17 shown in FIG. 17 to some or greater extent throughout. However, the reconstructed image P19 fails to render a part of the relatively low contrast structures rendered in light gray in the reconstructed image P17.

Figure 20:
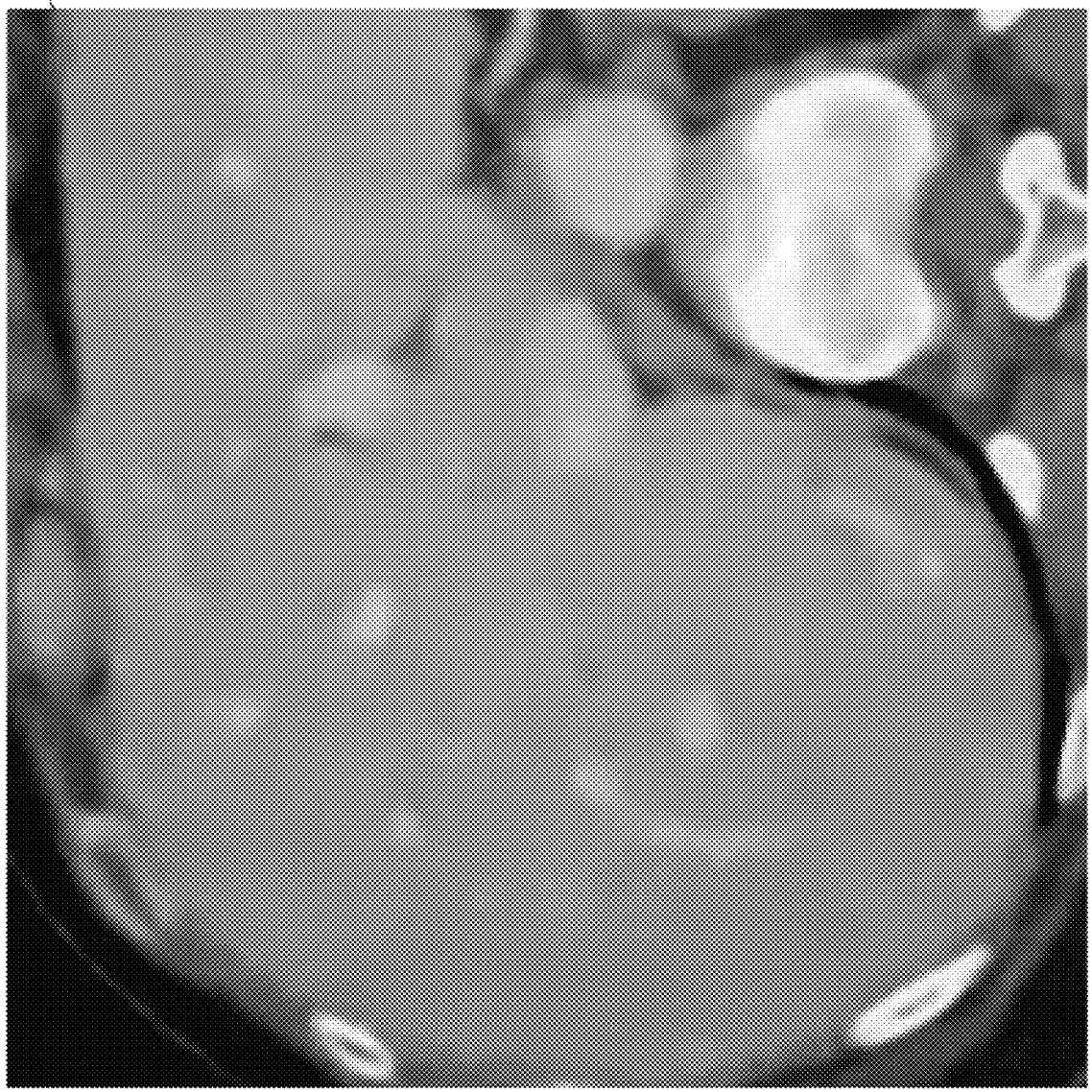
FIG. 20 is a diagram showing an example of a reconstructed image generated using a trained model generated by inputting first input image data and second input image data to the machine learning device according to the embodiment.

FIG. 20 is a diagram showing an example of a reconstructed image generated using a trained model generated by inputting first input image data and second input image data to a machine learning device according to the embodiment. A reconstructed image P20 shown in FIG. 20 is generated from projection data of 64 directions acquired by sparse-view CT imaging. As shown in the lower left of FIG. 20, the reconstructed image P20 has an image evaluation index of 0.902.

The reconstructed image P20 shown in FIG. 20 reproduces smooth density changes and fine textures rendered in the reconstructed image P17 shown in FIG. 17 with high accuracy throughout. In the reconstructed image P20, relatively low contrast structures are rendered in light gray to the same extent as in the reconstructed image P17 shown in FIG. 17. In the reconstructed images shown in FIGS. 18 to 21, the reconstructed image P20 is second closest to the reconstructed image P17 shown in FIG. 17.

Figure 21:
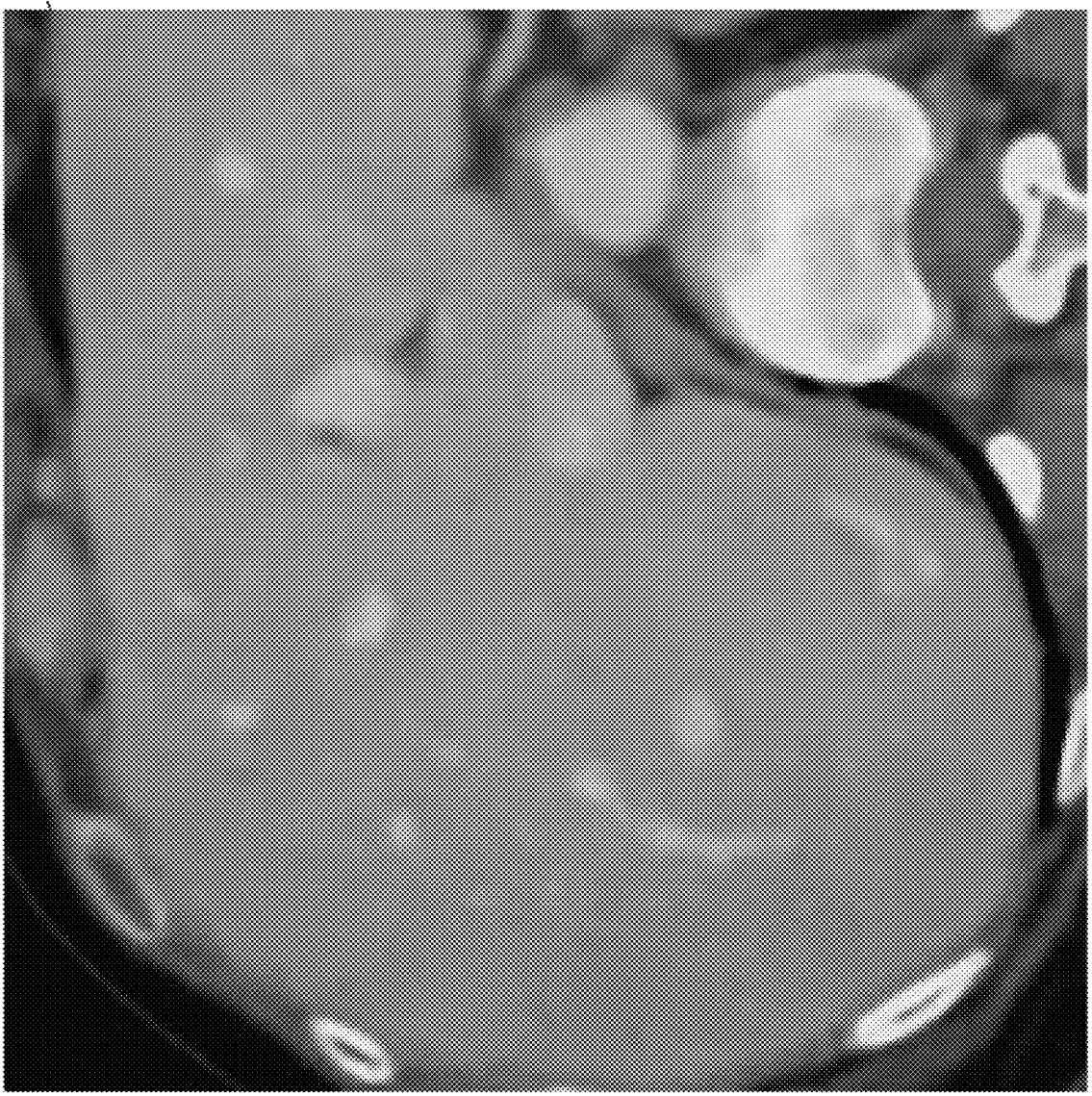
FIG. 21 is a diagram showing an example of a reconstructed image generated using a trained model generated by inputting a plurality of pieces of first input image data to the machine learning device and inputting a piece of second input image data to the machine learning device according to the embodiment.

FIG. 21 is a diagram showing an example of a reconstructed image generated using a trained model generated by inputting a plurality of pieces of first input image data to a machine learning device and inputting a piece of second input image data to the machine learning device according to the embodiment. A reconstructed image P21 shown in FIG. 21 is generated from projection data of 64 directions acquired by sparse-view CT imaging. As shown in the lower left of FIG. 21, the reconstructed image P21 has an image evaluation index of 0.910.

The reconstructed image P21 shown in FIG. 21 reproduces smooth density changes and fine textures rendered in the reconstructed image P17 shown in FIG. 17 with high accuracy throughout. In the reconstructed image P21, relatively low contrast structures are rendered in light gray to the same extent as in the reconstructed image P17 shown in FIG. 17. In the reconstructed images shown in FIGS. 18 to 21, the reconstructed image P21 is closest to the reconstructed image P17 shown in FIG. 17.

The reconstructed image P21 is closer to the reconstructed image P17 shown in FIG. 17 than the reconstructed image P20 is. The reason for this is that a desirable value of the smoothing parameter β differs depending on a location on the reconstructed image, and the first input image data with a desirable smoothing parameters β generated by the trained model is selected for each location on a reconstructed image, and the reconstructed image is generated by combining these various smoothing parameters β. That is, unlike the reconstructed image P20, the reconstructed image P21 is generated using a trained model generated by inputting a plurality of pieces of first input image data in which different smoothing parameters β are set and thus is closer to the reconstructed image P17 shown in FIG. 17 than the reconstructed image P20 is.

Although the above embodiment has been described with respect to the case where the trained model generation device 30 and the image generation device 40 are separate as an example, the present invention is not limited to this. That is, the trained model generation device 30 and the image generation device 40 may be formed as an integrated device.

Although the above embodiment has been described with respect to the case where the machine learning device 50 generates a trained model that uses a convolutional neural network as an example, the present invention is not limited to this. The machine learning device 50 may generate, for example, a trained model that uses a recurrent neural network (RNN).

Although the above embodiment has been described with respect to the case where the trained model generation program 300 does not input second input image data to the machine learning device 50 in the third processing as an example, the present invention is not limited to this. The trained model generation program 300 may input a piece of second input image data to the machine learning device 50 together with at least two types of first input image data and a piece of output image data in the third processing.

Although the above embodiment has been described with respect to the case where the trained model generation program 300 inputs output image data to the machine learning device 50 and causes the machine learning device 50 to perform supervised learning when performing any of the first processing, the second processing, or the third processing as an example, the present invention is not limited to this. That is, the trained model generation program 300 may cause the machine learning device 50 to perform unsupervised learning without inputting output image data to the machine learning device 50 when performing the first processing, the second processing, or the third processing.

Although the above embodiment has been described with respect to the case where the functions illustrated in FIG. 1 are each implemented by a hardware processor that loads and executes the trained model generation program 300 as an example, the present invention is not limited to this. At least some of the functions illustrated in FIG. 1 may be implemented by hardware including circuitry such as a large scale integration (LSI), an application specific integrated circuit (ASIC), a field-programmable gate array (FPGA), and a graphics processing unit (GPU). Alternatively, at least some of the functions illustrated in FIG. 1 may be implemented by software and hardware in cooperation. These pieces of hardware may be integrated into one unit or may be divided into a plurality of parts.

Although the above embodiment has been described with respect to the case where the trained model generation program 300 and the image generation program 400 are applied to reconstructed images generated by the X-ray CT device as an example, the present invention is not limited to this. The trained model generation program 300 and the image generation program 400 can also be applied, for example, to reconstructed images generated by a positron emission tomography (PET) device, a single photon emission computed tomography (SPECT) device, or a magnetic resonance imaging (MRI) device.

Embodiments of the present invention have been described in detail above with reference to the drawings. However, the specific configurations of the embodiments of the present invention are not limited to those of the embodiments and may be those of the above embodiments to which at least one of various combinations, modifications, replacements, or design changes has been made without departing from the spirit of the present invention.

REFERENCE SIGNS LIST

1 Image generation system
10 X-ray CT device
20 Storage device
30 Trained model generation device
300 Trained model generation program
310 Learning execution function
320 Trained model acquisition function
40 Image generation device
400 Image generation program
410 Image generation function
50 Machine learning device

What is claimed is:

1. A non-transitory computer-readable storage medium storing a trained model generation program causing a computer to implement:
a learning execution function of:
inputting first input image data representing a first input image generated by a first reconstruction method using compressed sensing and second input image data representing a second input image generated by a second reconstruction method different from the first reconstruction method to a machine learning device to execute machine learning, the second reconstruction method being an analytical reconstruction method, and
causing the machine learning device to generate a trained model; and
a trained model acquisition function of acquiring trained model data indicating the trained model,
wherein the learning execution function searches for a smoothing parameter of the first reconstruction method, a weight used in a convolutional neural network that is used as the trained model, and a bias used in the convolutional neural network which minimize a mean squared error to cause the machine learning device to generate the trained model.

2. The non-transitory computer-readable storage medium according to claim 1, wherein the learning execution function searches for the smoothing parameter, the weight, and the bias which minimize the mean squared error represented by the following equation (1) to cause the machine learning device to generate the trained model:

[Math. 1]

$$MSE(w, b, \beta) = \frac{1}{N}\sum_{i=1}^{N}\left\|x_i - CNN(w, b)\begin{bmatrix}y_i\\z_i(\beta)\end{bmatrix}\right\|^2 \quad (1)$$

where w is a vector in which weights used in the convolutional neural network are arranged in a row, b is a vector in which biases used in the convolutional neural network are arranged in a row, $\beta$ is a smoothing parameter of the first reconstruction method, $x_i$ is a vector in which values indicating densities represented by pixels of an output image are arranged in a row, $y_i$ is a vector in which values indicating densities represented by pixels of the second input image are arranged in a row, and $z_i$ is a vector in which values indicating densities represented by pixels of the first input image are arranged in a row.

3. The non-transitory computer-readable storage medium according to claim 1, wherein the learning execution function:

inputs to the machine learning device at least the first input image data representing the first input image generated by the first reconstruction method using the compressed sensing configured with a first smoothing parameter and the first input image data representing the first input image generated by the first reconstruction method using the compressed sensing configured with a second smoothing parameter having a different value from the first smoothing parameter, and causes the machine learning device to perform machine learning and generate the trained model.

4. The non-transitory computer-readable storage medium according to claim 1, wherein the learning execution function:

inputs to the machine learning device output image data representing an output image generated by a third reconstruction method different from the first reconstruction method, in addition to the first input image data, and causes the machine learning device to perform machine learning and generate the trained model.

5. An image generation program causing a computer to implement an image generation function of inputting input image data representing an input image to the trained model generated by the trained model generation program according to claim 1 to generate a reconstructed image.

6. A trained model generation device comprising:

a processor configured to:

input to a machine learning device first input image data representing a first input image generated by a first reconstruction method using compressed sensing and second input image data representing a second input image generated by a second reconstruction method different from the first reconstruction method, the second reconstruction method being an analytical reconstruction method;

cause the machine learning device to perform machine learning and generate a trained model; and acquire trained model data indicating the trained model, wherein the processor is configured to search for a smoothing parameter of the first reconstruction method, a weight used in a convolutional neural network that is used as the trained model, and a bias used in the convolutional neural network which minimize a mean squared error to cause the machine learning device to generate the trained model.

7. An image generation device comprising:

a processor configured to input input image data representing an input image to the trained model generated by the trained model generation device according to claim 6 to generate a reconstructed image.

8. A trained model generation method comprising:

inputting to a machine learning device first input image data representing a first input image generated by a first reconstruction method using compressed sensing and second input image data representing a second input image generated by a second reconstruction method different from the first reconstruction method, the second reconstruction method being an analytical reconstruction method;

causing the machine learning device to perform machine learning and generate a trained model; and acquiring trained model data indicating the trained model, wherein the method includes searching for a smoothing parameter of the first reconstruction method, a weight used in a convolutional neural network that is used as the trained model, and a bias used in the convolutional neural network which minimize a mean squared error to cause the machine learning device to generate the trained model.

9. An image generation method comprising inputting input image data representing an input image to the trained model generated by the trained model generation method according to claim 8 to generate a reconstructed image.

10. A non-transitory computer-readable storage medium storing a trained model generation program causing a computer implement:

a learning execution function of:

inputting first input image data including more than two first input images generated by a first reconstruction method using compressed sensing and second input image data including a second input image generated by a second reconstruction method different from the first reconstruction method to a machine learning device to execute machine learning, the second reconstruction method being an analytical reconstruction method, and causing the machine learning device to generate a trained model; and a trained model acquisition function of acquiring trained model data indicating the trained model, wherein the more than two first input images are configured with different smoothing parameters from each other, and wherein the learning execution function searches for a smoothing parameter of the first reconstruction method, a weight used in a convolutional neural network that is used as the trained model, and a bias used in the convolutional neural network which minimize a mean squared error to cause the machine learning device to generate the trained model.

* * * * *